(12) United States Patent
Radl et al.

(10) Patent No.: US 7,942,866 B2
(45) Date of Patent: May 17, 2011

(54) DEVICE FOR TREATING A WOUND

(75) Inventors: Christopher L. Radl, Malvern, PA (US); John R. Boehringer, Wynnewood, PA (US); John Karpowicz, Chester Springs, PA (US); Jacob L. Timm, Hancock, NH (US)

(73) Assignee: Boehringer Technologies, L.P., Phoenixville, PA (US)

( * ) Notice: Subject to any disclaimer, the term of this patent is extended or adjusted under 35 U.S.C. 154(b) by 0 days.

(21) Appl. No.: 10/928,942

(22) Filed: Aug. 27, 2004

(65) Prior Publication Data

US 2005/0101940 A1    May 12, 2005

Related U.S. Application Data

(63) Continuation-in-part of application No. 10/663,226, filed on Sep. 16, 2003, now Pat. No. 7,815,616.

(60) Provisional application No. 60/498,521, filed on Aug. 28, 2003.

(51) Int. Cl.
*A61M 27/00* (2006.01)
*A61M 1/00* (2006.01)
*A61F 5/44* (2006.01)

(52) U.S. Cl. ......... 604/543; 604/334; 604/355; 604/317

(58) Field of Classification Search .................. 604/543, 604/133, 334, 355, 118, 119, 305, 318, 122, 604/317, 27
See application file for complete search history.

(56) References Cited

U.S. PATENT DOCUMENTS

| 679,918 A | 8/1901 | Shears |
|---|---|---|
| 697,637 A | 4/1902 | Lee |
| 720,812 A | 2/1903 | Johnson |
| 843,674 A | 2/1907 | Funk |
| 1,066,934 A | 7/1913 | Manney |
| 1,251,258 A | 12/1917 | Magill |
| 1,355,679 A | 10/1920 | McConnel |
| 1,385,346 A | 7/1921 | Taylor |
| 2,025,492 A | 12/1935 | Aird |
| 2,113,253 A | 4/1938 | Gray |
| 2,122,121 A | 6/1938 | Tillotson |

(Continued)

FOREIGN PATENT DOCUMENTS

EP    0 619 105 A1    10/1994

(Continued)

OTHER PUBLICATIONS

Dewan, "An Alternative Approach to Skin Graft Donor Site Dressing," Jun. 1986. 2 pages.

(Continued)

*Primary Examiner* — Jacqueline F. Stephens
(74) *Attorney, Agent, or Firm* — Caesar, Rivise, Bernstein, Cohen & Pokotilow, Ltd.

(57) ABSTRACT

A medical device that seals a wound and facilitates wound drainage with suction is provided. In one exemplary embodiment, the device comprises a suction portion, having both an inlet valve and an outlet valve, for suctioning fluids from the wound, and a sealing portion for sealing the wound by engaging the skin adjacent the wound, the suction portion and sealing portion being integral with one another. A method for draining a wound comprises the steps of under-packing the wound with a packing material; sealing the wound; and applying suction to the wound to promote wound drainage and to promote intimate contact between the wound and the packing material.

4 Claims, 6 Drawing Sheets

U.S. PATENT DOCUMENTS

| | | |
|---|---|---|
| 2,195,771 A | 4/1940 | Estler |
| 2,280,915 A | 4/1942 | Johnson |
| 2,367,690 A | 1/1945 | Purdy |
| 2,385,207 A | 9/1945 | Hunn |
| 2,524,750 A | 10/1950 | Bellinger |
| 2,727,678 A | 12/1955 | Henderson |
| 3,026,874 A | 3/1962 | Stevens |
| 3,042,041 A | 4/1962 | Jascalevich |
| 3,042,037 A | 7/1962 | Scales |
| 3,288,140 A | 11/1966 | McCarthy |
| 3,367,332 A | 2/1968 | Groves |
| 3,397,648 A | 8/1968 | Henderson |
| 3,398,743 A | 8/1968 | Shalit |
| 3,486,504 A | 12/1969 | Austin |
| 3,556,096 A | 1/1971 | Fuller |
| 3,568,675 A | 3/1971 | Harvey |
| 3,599,639 A | 8/1971 | Spotz |
| 3,610,238 A | 10/1971 | Rich |
| 3,616,156 A | 10/1971 | Scholl |
| 3,874,387 A | 4/1975 | Barbieri |
| 3,933,158 A | 1/1976 | Haverstock |
| 3,954,105 A | 5/1976 | Nordby |
| RE29,319 E | 7/1977 | Nordby |
| 4,080,970 A | 3/1978 | Miller |
| 4,112,947 A | 9/1978 | Nehring |
| 4,180,074 A | 12/1979 | Murry |
| 4,224,941 A | 9/1980 | Stivala |
| 4,224,945 A | 9/1980 | Cohen |
| 4,250,882 A | 2/1981 | Adair |
| 4,261,363 A | 4/1981 | Russo |
| 4,341,208 A | 7/1982 | Gordon |
| 4,382,441 A | 5/1983 | Svedman |
| 4,392,858 A * | 7/1983 | George et al. .................. 604/133 |
| 4,399,816 A | 8/1983 | Spangler |
| 4,444,548 A | 4/1984 | Anderson et al. |
| 4,465,062 A | 8/1984 | Versaggi et al. |
| 4,533,352 A | 8/1985 | Van Beek et al. |
| 4,551,141 A | 11/1985 | McNeil |
| 4,553,967 A | 11/1985 | Ferguson et al. |
| 4,641,643 A | 2/1987 | Greer |
| 4,710,165 A | 12/1987 | McNeil et al. |
| 4,717,382 A | 1/1988 | Clemens |
| 4,743,232 A | 5/1988 | Kruger |
| 4,778,446 A | 10/1988 | Jensen |
| 4,795,435 A | 1/1989 | Steer |
| 4,820,284 A | 4/1989 | Hauri |
| 4,925,447 A | 5/1990 | Rosenblatt |
| 4,941,882 A | 7/1990 | Ward |
| 4,969,880 A | 11/1990 | Zamierowaski |
| 4,969,881 A | 11/1990 | Viesturs |
| 5,014,389 A | 5/1991 | Ogilvie |
| 5,019,059 A | 5/1991 | Goldberg et al. |
| 5,034,006 A | 7/1991 | Hosoda |
| 5,086,763 A | 2/1992 | Hathman |
| 5,088,483 A | 2/1992 | Heinecke |
| 5,100,396 A | 3/1992 | Zamierowski |
| 5,106,362 A | 4/1992 | Gilman |
| 5,149,331 A | 9/1992 | Ferdman et al. |
| 5,152,757 A | 10/1992 | Eriksson |
| 5,160,315 A | 11/1992 | Heinecke |
| 5,161,544 A | 11/1992 | Morris |
| 5,167,613 A | 12/1992 | Karami |
| 5,176,663 A | 1/1993 | Svedman |
| 5,244,457 A | 9/1993 | Karami |
| 5,261,893 A | 11/1993 | Zamierowski |
| 5,358,494 A | 10/1994 | Svedman |
| 5,437,651 A | 8/1995 | Todd |
| 5,437,683 A | 8/1995 | Neumann |
| 5,447,505 A | 9/1995 | Valentine |
| D364,679 S | 11/1995 | Heaton et al. |
| 5,480,030 A | 1/1996 | Sweeney |
| 5,484,399 A | 1/1996 | DiResta |
| 5,527,293 A | 6/1996 | Zamierowski |
| 5,549,584 A * | 8/1996 | Gross .......................... 604/313 |
| 5,562,107 A | 10/1996 | Lavender et al. |
| 5,636,643 A | 6/1997 | Argenta |
| 5,645,081 A | 7/1997 | Argenta |
| 5,701,917 A | 12/1997 | Khouri |
| 5,840,049 A | 11/1998 | Turney |
| 5,848,998 A | 12/1998 | Marasco, Jr. |
| D406,899 S | 3/1999 | Cottle |
| 5,931,797 A | 8/1999 | Turney et al. |
| 5,951,533 A | 9/1999 | Freeman |
| 6,071,267 A | 6/2000 | Zamierowaski |
| 6,116,781 A | 9/2000 | Skeens |
| 6,117,111 A | 9/2000 | Fleischmann |
| 6,135,116 A | 10/2000 | Vogel |
| 6,142,982 A | 11/2000 | Hunt |
| 6,174,306 B1 | 1/2001 | Fleischmann |
| 6,203,563 B1 | 3/2001 | Fernandez |
| 6,242,665 B1 | 6/2001 | Malowaniec |
| 6,283,931 B1 | 9/2001 | Augustine |
| 6,323,386 B1 | 11/2001 | Stapf et al. |
| 6,345,623 B1 | 2/2002 | Heaton et al. |
| 6,458,109 B1 | 10/2002 | Henley et al. |
| 6,557,704 B1 | 5/2003 | Randolph |
| 2001/0020146 A1 | 9/2001 | Satterfield |
| 2001/0029956 A1 | 10/2001 | Argenta |
| 2001/0031943 A1 | 10/2001 | Urie |
| 2001/0043943 A1 | 11/2001 | Coffey |
| 2002/0016577 A1 | 2/2002 | Ohmstede |
| 2002/0017304 A1 | 2/2002 | Heaton et al. |
| 2002/0065494 A1 | 5/2002 | Lockwood et al. |
| 2002/0068913 A1 | 6/2002 | Fleischmann |
| 2002/0120185 A1 | 8/2002 | Johnson |
| 2002/0143286 A1 | 10/2002 | Tumey |
| 2003/0040687 A1 | 2/2003 | Boynton et al. |
| 2003/0219469 A1 | 11/2003 | Johnson et al. |
| 2004/0064132 A1 * | 4/2004 | Boehringer et al. .......... 604/543 |
| 2004/0260230 A1 * | 12/2004 | Randolph ..................... 604/28 |
| 2006/0079852 A1 * | 4/2006 | Bubb et al. ................... 604/317 |

FOREIGN PATENT DOCUMENTS

| | | |
|---|---|---|
| EP | 0 853 950 A1 | 7/1998 |
| EP | 0 777 504 B1 | 10/1998 |
| GB | 606248 | 8/1948 |
| GB | 641061 | 8/1950 |
| GB | 1395799 | 5/1975 |
| GB | 1549756 | 8/1979 |
| GB | 2 099 308 A | 12/1982 |
| GB | 2 307 180 A | 11/1995 |
| GB | 2 329 127 A | 3/1999 |
| GB | 2 333 965 A | 8/1999 |
| GB | 2 336 546 A | 10/1999 |
| GB | 2 351 025 A | 12/2000 |
| GB | 2 356 148 A | 5/2001 |
| GB | 2 365 350 A | 2/2002 |
| WO | WO 80/01139 | 6/1980 |
| WO | WO 89/05133 | 6/1989 |
| WO | WO 91/00718 | 1/1991 |
| WO | WO 96/05873 | 2/1996 |
| WO | WO 98/17329 | 4/1998 |
| WO | WO 00/21586 | 4/2000 |
| WO | WO 00/59418 | 10/2000 |
| WO | WO 00/59424 | 10/2000 |
| WO | WO 01/34223 A1 | 5/2001 |
| WO | WO 01/37922 A1 | 5/2001 |
| WO | WO 01/85248 A1 | 11/2001 |

OTHER PUBLICATIONS

Alexander, "Bacteriologic Comparison of Closed Suction and Penrose Drainage," Nov. 1984. 1 page.

Genecov, "A Controlled Subatmospheric Pressure Dressing Increases the Rate of Skin Graft Donor Site Reepithelialization," Mar. 1998. 7 pages.

Biblehimer, "Dealing With a Wound That Drains 1.5 Liters A Day," Aug. 1986. 3 pages.

Fay, "Drainage Systems: Their Role in Wound Healing," Sep. 1987. 10 pages.

Fredman, "Dressing System Providing Fluid Supply and Suction Drainage Used for Continuous or Intermittent Irrigation," Aug. 1986. 8 pages.

Morykwas, "Effects of Varying Levels Subatmospheric Pressure on the Rate of Granulation Tissue Formation in Experimental Wounds in Swine," Nov. 2003. 5 pages.

Alexander, "Emerging Concepts in the Control of Surgical Infections," Jun. 1974. 13 pages.
Hathman Medical Products. 1 page.
Pescovitz, "A History of Surgical Suction From Dieulafoy to Gomoco," Sep. 1989. 9 pages.
Fowler, "How to Cope When Your Patient Has an Entercutaneous Fistula," Mar. 1990. 4 pages.
Landes, "An Improved Suction Device for Draining Wounds," May 1972. 1 page.
Shaer, "Inexpensive Vacuum-assisted Closure Employing a Conventional Disposable Closed-suction Drainage System," Jan. 2003. 2 pages.
Arnljots, "Irrigation Treatment in Split-Thickness Grafting of Intractable Leg Ulcers," 1985. 3 pages.
Svedman, "Irrigation Treatment of Leg Ulcers," Sep. 1983. 3 pages.
Jeter, "New and Established Methods; Managing Draining Wounds and Fistulae," 1990. 7 pages.
Nakayama, "A New Method for the Dressing of Free Skin Grafts," Dec. 1900. 4 pages.
Rabinovici, "New Sump Suction Appliance for Drainage of Enterocutaneous Fistulae," May 1988. 1 page.
Abramson, "A New, Soft, Triple Lumen, Overflow and Suction Drain," Sep. 1970. 3 pages.
Ramirez, "Optimal Wound Healing under Op-Site Dressing," Mar. 1973. 2 pages.
Bellinger, An Original Drainage Cup Apparatus for Ileostomies and Fistullas,: Nov. 1949. 5 pages.
Alexander, "Prevention of Wound Infections-A Case for Closed Drainage to Remove Wound Fluids Deficient in Opsonic Protein," Jul. 1976. 5 pages.
Gramm, "Respiratory Controlled Intermittent Inspiratory Pleural Drainage," Oct. 1984. 1 page.
Schein, "'Sandwich Technique' in the Management of the Open Abdomen," May 1986. 2 pages.
"Sternal Dehiscence 'Delayed Primary Closure' for Complicated Cases," 1981. 3 pages.
Hentzer, "Suction Blister Transplantation for Leg Ulcers," 1975. 3 pages.
Furnas, "Suction Catheters for Open Technique of Skin Grafting in Fresh Wounds," Oct. 1976. 1 page.
Jascalevich, "Suction Cone: A New Apparatus for the Care of Ileostomies, Fistulas and Draining Sinuses," Sep. 1960. 4 pages.
Silvis, "The Use of Continuous Suction Negative Pressure Instead of Pressure Dressing," Aug. 1955. 5 pages.
Morykwas, "Use of a Subatmospheric Pressure to Prevent Doxorubicin Extravasation Ulcers in a Swine Model," Jun. 1999. 4 pages.
Morykwas, "Use of a Subatmospheric Pressure to Prevent Progression of Partial-Thickness Burns in a Swine Model," Jan. 1999. 7 pages.
Vieira, "Vacuum Assisted Closure in Calcanectomy for the Treatment of Chronic Calcaneal Osteomyelitis," Jun. 1997. 2 pages.
Barker, "Vacuum Pack Technique of Temporary Abdominal Closure: A 7 Year Experience with 112 Patients," Feb. 2000. 6 pages.
Argenta, "Vacuum-Assisted Closure: A New Method for Wound Control and Treatment: Clinical Experience," Jun. 1997. 15 pages.
US 6,216,701, 04/2001, Heaton (withdrawn)

* cited by examiner

DEVICE FOR TREATING A WOUND

This application claims priority to provisional application No. 60/498,521, filed Aug. 28, 2003. This application is also a Continuation-in-Part of application Ser. No. 10/663,226 filed on Sep. 16, 2003.

FIELD OF THE INVENTION

This invention relates to a device and method for treating wounds. More particularly this invention relates to a device and method for treating wounds with suction.

BACKGROUND OF THE INVENTION

In the medical field there are many types of wounds that require treatment. In some instances they are post-operative wounds, but in other instances they can be open wounds that cannot yet be closed, as where infection sites exist, where open wounds require periodic application of medicine, or where the wounds are chronic non-healing pressure ulcers, venous ulcers, diabetic ulcers or where the wounds are too large to close surgically and must be allowed to heal on their own. In such cases, it is known that it can be desirable from the point of wound treatment, to apply a negative pressure or suction to the wound to remove fluids and exudates from the wound.

SUMMARY OF THE INVENTION

To overcome the deficiencies of conventional wound treatment techniques and devices, the present invention is a medical device that seals a wound and facilitates wound drainage with suction. In one exemplary embodiment of the present invention, the device comprises a suction means, having both an inlet valve and an outlet valve, for suctioning fluids from the wound, and a sealing means for sealing the wound by engaging the skin adjacent the wound, the suction means and sealing means being integral with one another.

According to one aspect of the present invention, the suction means comprises a one-way inlet valve, a one-way outlet valve, a housing comprised of one or more flexible sheets and a resilient foam contained within the housing. The sealing means is comprised of an adhesive backed flexible sheet where at least a portion of the adhesive backed sheet forms part of the housing of the suction means.

In another exemplary embodiment of the present invention, the device comprises a suction means for suctioning fluid from a wound, a primary sealing means for sealing the wound by engaging the skin adjacent the wound and a gap filling means attached to a portion of the sealing means, where the gap filling means substantially conforms to and/or fills irregularities in the skin surrounding the wound as well as irregularities in the sealing means. In a preferred embodiment, the sealing means comprises an adhesive backed flexible sheet and the gap filling means comprises a generally non-resilient, non-memory, putty-like material.

In yet another exemplary embodiment, the invention comprises a suction means, a sealing means and a semi-flexible reinforcement means that serves to reinforce the sealing means such that the suction forces applied to the wound are generally greater than those that would be applied in the absence of the reinforcement means, thereby increasing wound drainage. Desirably, the sealing means is a thin, generally conformable adhesive backed polymer sheet and the reinforcement means is a generally thicker polymer sheet that is attached to the thin adhesive backed polymer sheet.

In another exemplary embodiment, the invention comprises a suction means, a sealing means and a semi-flexible cover means. Desirably, the semi-flexible cover means is comprised of a sheet of polyurethane having a thickness of about 0.025" and the sealing means is comprised of a flange of adhesive backed polyurethane film having a thickness of about 0.002" with the flange being attached to the perimeter of the cover means.

The present invention also includes a method of treating a wound comprising the steps of under-packing a wound, sealing the wound and applying suction to the wound to promote intimate contact between the wound and the packing.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

This application is a Continuation-in-Part of application Ser. No. 10/663,226 filed on Sep. 16, 2003, the entire disclosure of which is incorporated herein by reference as if set forth in full.

Figure 1:
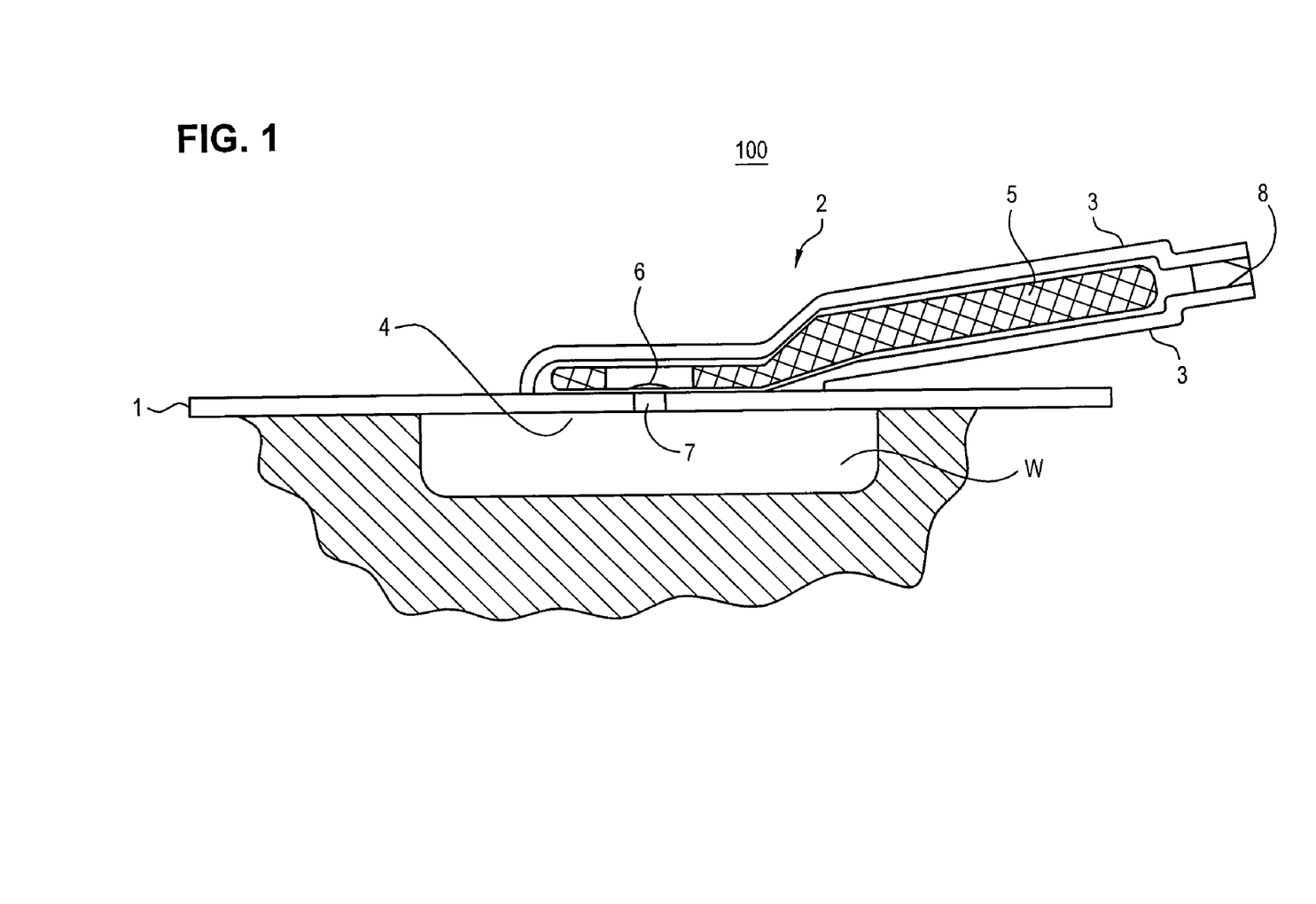
FIG. 1 is a cross sectional view of an exemplary embodiment of the present invention as applied to a wound.

A first exemplary embodiment of the present invention is illustrated in FIG. 1. As shown in FIG. 1, device 100 includes a sealing means comprised of an adhesive backed flexible sheet 1 for sealing wound W and a suction source 2 for suctioning waste fluids from the wound W. Although suction source 2 is shown as self contained and may be desirable for certain implementations, the invention is not so limited. In one exemplary embodiment, suction source 2 and the adhesive backed flexible sheet 1 are integral to one another, forming a complete self-contained compact unit that can be easily applied to wounds that require suction drainage.

Flexible sheet 1 is desirably an adhesive backed flexible sheet, such as 3M™ product number 9841 available from 3M™ Company of St. Paul, Minn. 3M™ 9841 includes a thin semi-permeable polyurethane film and a biocompatible adhesive backing. Flexible sheet 1 has a thickness of about 0.002". By virtue of its semi-permeability some water vapor can permeate out through the sheet. At the same time, a seal is maintained so that suction can be applied to the wound W. Semi-permeability is well known to those skilled in the art.

Suction Source

In one exemplary embodiment, suction source 2 is comprised of a housing fabricated from flexible films 3 and portion 4 of the adhesive backed flexible sheet 1. The films 3 are desirably polyurethane and can be joined to one another by RF welding or other conventional joining means, as well as to the adhesive backed flexible sheet 1. Contained within the housing of suction source 2 is a resilient element 5 that springs back after compression. In one exemplary embodiment, resilient element 5 is an open-cell foam. In one exemplary embodiment, suction source 2 comprises an inlet valve 6 and an outlet valve 8. Valves 6 and 8 are both one-way valves that permit fluids to move in one direction only. Specifically, valve 6 permits fluid to be draw toward suction source 2 while valve 8 permits fluid to be expelled from suction source 2.

When suction source 2 is compressed either by hand or any other means, air and/or liquids are expelled from the volume within the suction source 2 through outlet valve 8. When the compressing force is released from the suction source 2 the resilient element 5 expands and creates suction within suction source 2. This suction then draws fluids from wound W through opening 7 in adhesive backed flexible sheet 1 and through inlet valve 6. Suction source 2 can be compressed multiple times as desired until the space defined by the wound is evacuated as desired, either partially or completely. At this point, resilient element 5 will remain compressed and maintain a vacuum in suction source 2. The compressed state is illustrated in FIG. 2.

Figure 2:
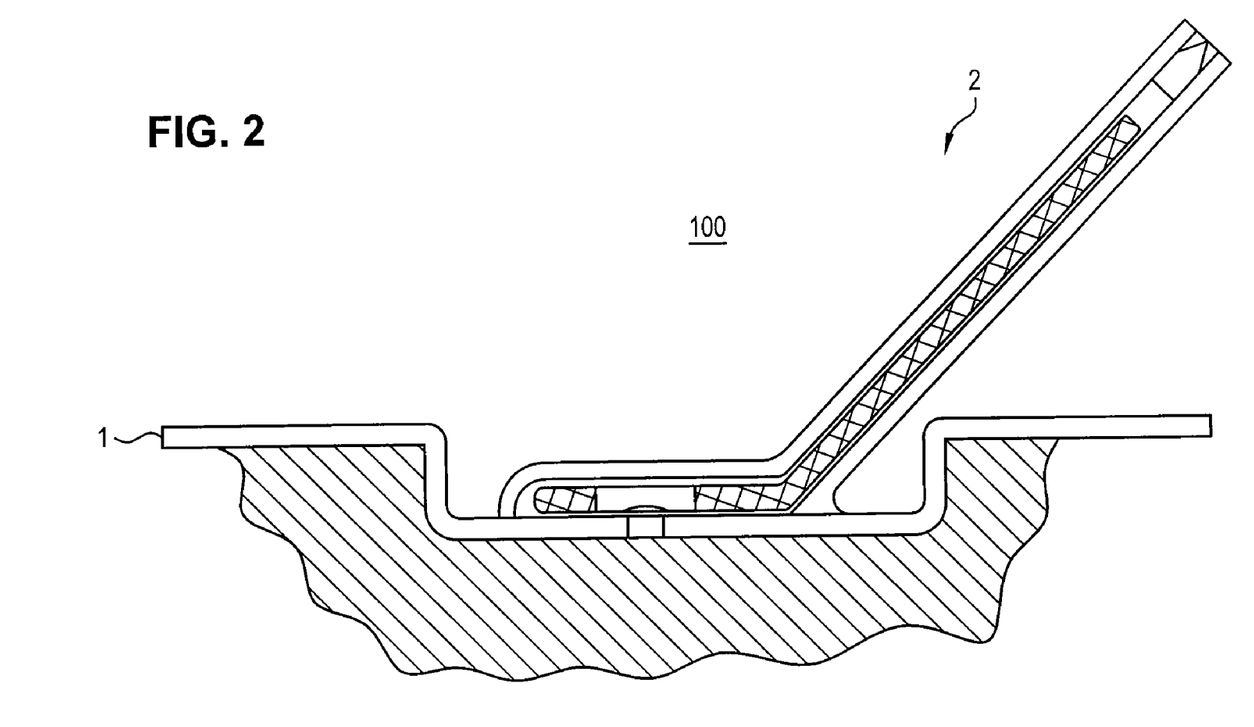
FIG. 2 is a cross sectional view of the exemplary device applied to a wound after the suction source has been actuated.

As shown in FIG. 2, the resilient element 5 is compressed and all fluids have been removed from the wound. Further, adhesive backed flexible sheet 1 has been drawn into intimate contact with the wound W. As new fluids enter the area of the wound the suction source continues to draw fluids out of the area of the wound. These fluids may be various bodily fluids, such as blood, pus or wound exudates, or if a delivery system is used with the invention, the fluid could be a fluid that is delivered to the wound, such as to clean or otherwise treat the wound, for example. As fluid enters suction source 2, resilient element 5 will expand as the amount of suction decreases. If suction source 2 is allowed to completely fill with fluids, a vacuum will no longer exist in the suction source, and no additional fluids will be removed from the wound. Desirably, the suction source is compressed again before it completely fills so that fluids can continually be drawn from the wound. Fluids collected in the suction source are again expelled through outlet valve 8.

In an alternate embodiment, an external vacuum source may be coupled to suction source 2 to either provide periodic or constant suction, thus permitting less attention from the medical practitioner. Other suction sources may include a suction bulb or a spring loaded cylinder.

One-Way Valves

According to one exemplary embodiment of the present invention, valve 6 is comprised of a thin film of polyurethane. In one exemplary embodiment, the thickness of the thin film is about 0.001 inches. This thin film is partially joined to the adhesive backed flexible sheet 2 over opening 7. Fluids can thus pass from wound W into suction source 2 through opening 7. Fluid cannot flow in the opposite direction because such a flow would cause the film of valve 6 to seal around hole 7. Outlet valve 8 can be comprised of a ball and spring valve or a duckbill valve, for example. Those skilled in the art are familiar with both of these types of valves.

Gap Filling Material

Figure 3:
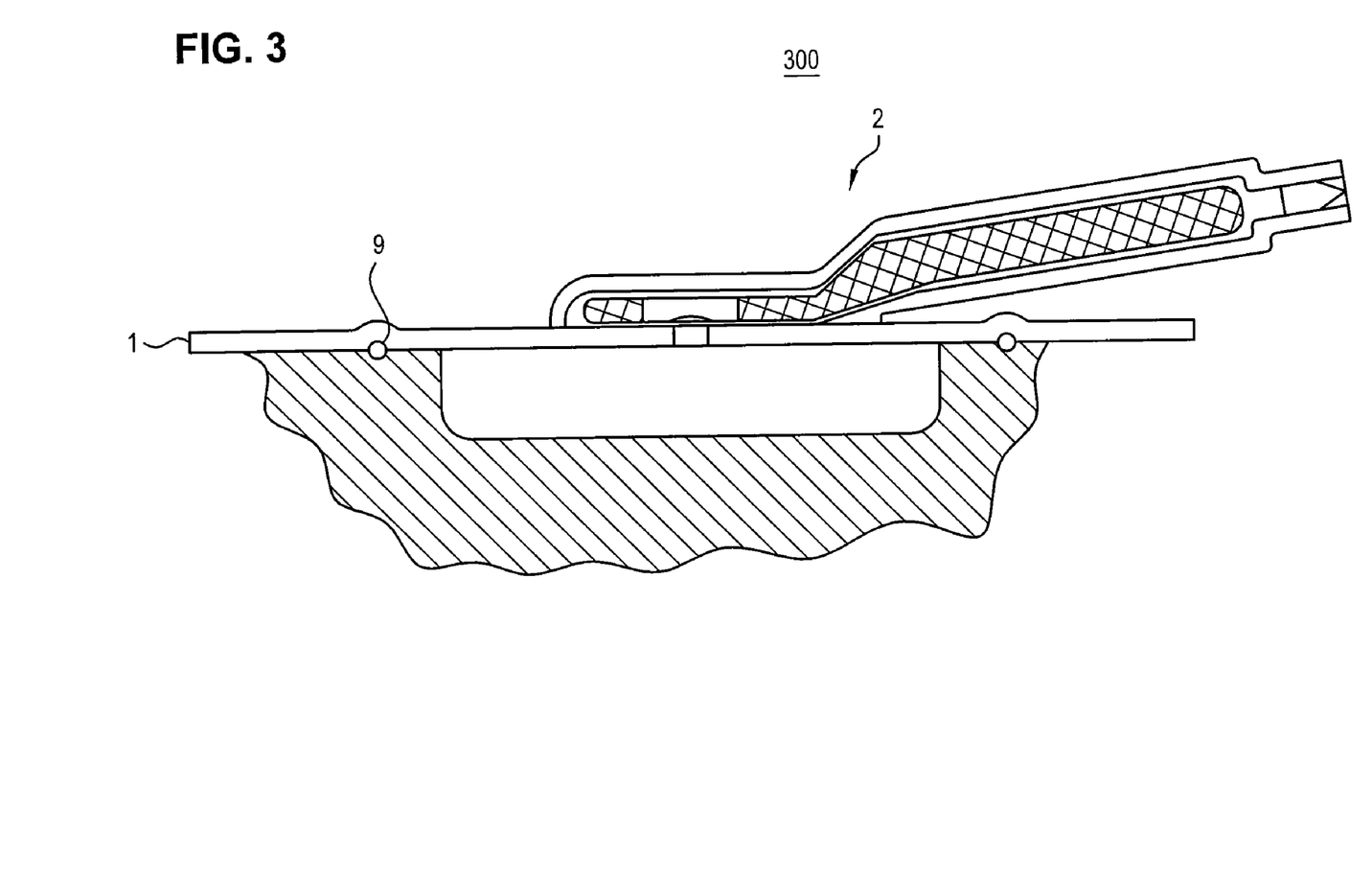
FIG. 3 is a cross sectional view of an exemplary embodiment of the present invention further comprising a gap filling material.

FIG. 3 illustrates an alternate embodiment of the present invention. As shown in FIG. 3, device 300 comprising adhesive backed flexible sheet 1, suction source 2 and gap filling material 9 disposed on a lower surface of flexible sheet 1. At times, a wound is located at a portion of the body that may be difficult to seal, such as at a joint or other locations with irregular surfaces including areas where there are skin folds. Thus, there may be small gaps between adhesive backed flexible sheet 1 and the skin surrounding wound W. These small gaps can form tiny leaks allowing air to leak into the area of the wound and into suction source 2. This reduces the time during which suction source 2 can maintain suction and increases the need to periodically compress suction source 2. A suitable gap filling material 9 can be incorporated into the invention. This gap filling material serves to fill any small gaps between the skin adjacent wound W and flexible sheet 1. In one exemplary embodiment, gap filling material 9 is a material made by Coloplast of Marietta, Georgia and marketed under the name Strip Paste. The paste is for use with ostomy pouches and is placed around an ostomy by the user to provide a flat smooth surface for attachment of the ostomy pouch. When used in the present invention, gap filling material 9 is incorporated in the device during manufacture. Desirably, a continuous bead of the gap filling material 9 is incorporated, so that when the invention is applied to a wound, a bead of gap filling material 9 is disposed between skin surrounding the wound W and sheet 1 as illustrated in FIG. 3. During assembly of the device gap filling material 9 can be extruded onto the adhesive backed side of sheet 1. Gap filling material 9 can then fill any gaps, including those caused by hairs, that might otherwise exist between the skin adjacent the wound W and sheet 1. The preferred gap filling material 9 has a number of important properties. Specifically, gap filling material 9 is not resilient, i.e. it generally does not have a memory and when it is pressed in to a gap it stays in the gap. Further, gap filling material 9 is biocompatible and stable, such that it can maintain its properties when incorporated into the invention and stored over a period of time prior to use.

Semi-Flexible Reinforcement

Figure 4:
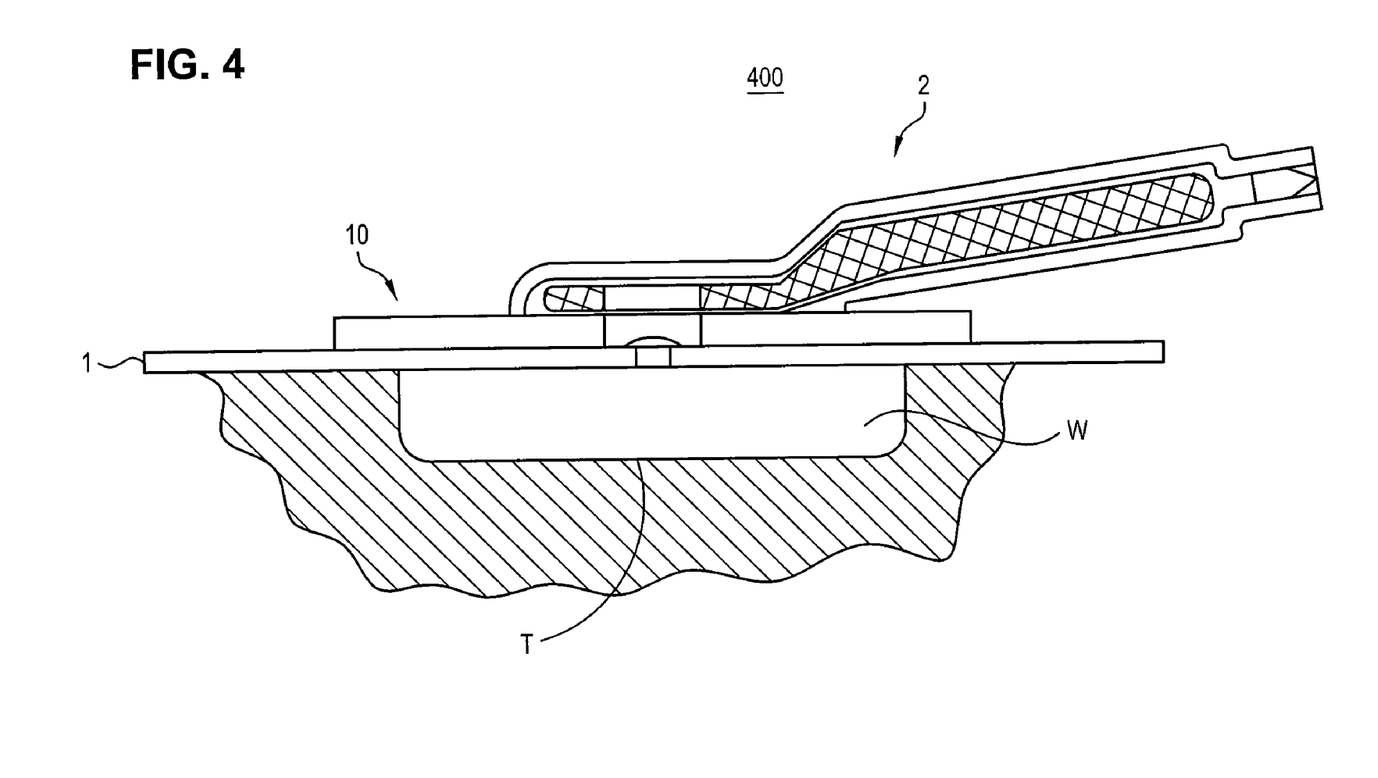
FIG. 4 is a cross sectional view of an exemplary embodiment of the present invention further comprising a reinforcing layer connected to the sealing means.
Figure 5:
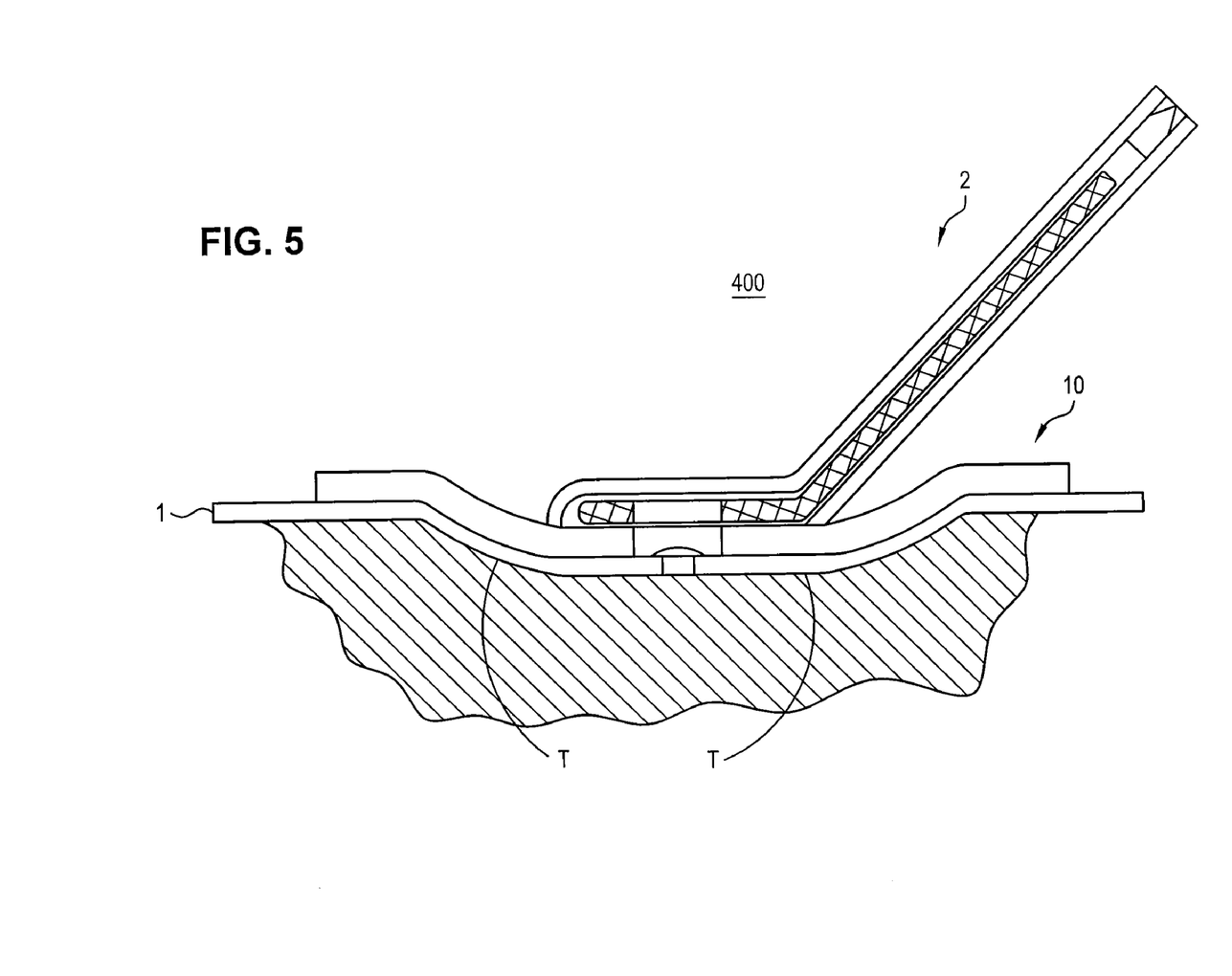
FIG. 5 is a cross sectional view of the invention with the reinforcement layer and the suction source actuated.

FIG. 4 illustrates another embodiment of the present invention. FIG. 4 shows device 400 prior to actuation of the suction source 2 and FIG. 5 shows device 400 with suction source 2 actuated. As illustrated in FIGS. 4 and 5, this exemplary embodiment of the present invention includes an adhesive backed flexible sheet 1, a suction source 2 and a semi-flexible reinforcement layer 10 disposed on an upper surface of flexible sheet 1. While adhesive backed flexible sheet 1 is desirably 3M product 9841, semi-flexible reinforcement layer 10 is desirably comprised of 0.025" thick polyurethane film, such as part number ST-1880 available from Stevens Urethane of Easthampton, Mass. The primary difference between this embodiment and that of FIGS. 1 and 2 is best illustrated by comparing FIGS. 2 and 5. The adhesive backed sheet 1 of FIG. 2 is extremely thin, compliant and stretchable. Therefore, when suction source 2 is actuated, sheet 1, by virtue of the generated suction, conforms nearly exactly to the surface of the wound W. In FIG. 5, semi-flexible layer 10 is joined to sheet 1 in a reinforcing fashion, such that when suction is generated, sheet 1 moves to conform only partially to the original contour of wound W. Simultaneously, tissue T of wound W moves to conform to sheet 1 as illustrated in FIG. 5. The net effect is that a greater force is applied to the wound W at a given suction level. This embodiment of the present invention is beneficial for those wounds where it may be desirable to achieve greater amounts of wound drainage and enhance contraction of the wound. It may also be beneficial to put openings (not shown) in semi-flexible layer 10, so that vapor passing through sheet 1 can pass through layer 10 as well.

Figure 6:
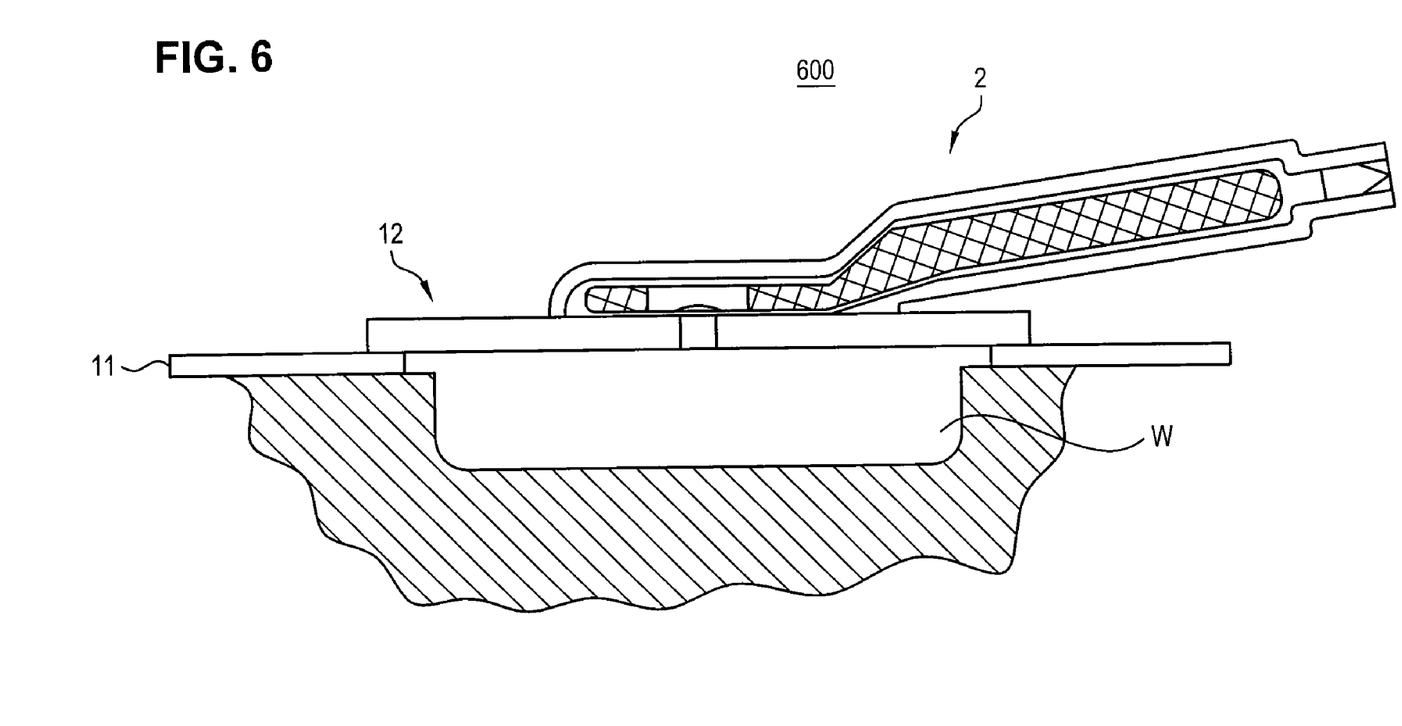
FIG. 6 is a cross sectional view of an exemplary embodiment of the present invention with a cover, a seal attached to the cover and a suction source attached to the cover.

FIG. 6 illustrates an alternate embodiment to that of FIG. 4. As shown in FIG. 6, device 600 comprises a suction source 2, a wound cover 12 and a seal 11 to be attached to the skin adjacent wound W. Seal 11 is desirably made from a section of 3M product 9841 cut to form a flange that is joined to a portion of the bottom surface of wound cover 12 (which is desirably a section of 0.025" thick Stevens polyurethane film 1880). In use, this embodiment behaves much like that of FIG. 4.

Wound Packing

For the treatment of some wounds it may be desirable to pack the wound with a wound packing material (not shown). One commonly used wound packing material is gauze, as well as others familiar to those skilled in the art. Wound packing materials are generally used to absorb fluids, aid in debridement and remove dead cells, bacteria or white cells for example, that have accumulated at the surface of the wound. The wound packing is generally changed periodically, and replaced with new fresh wound packing. Conventionally, packed wounds are packed so that the cavity is completely filled, ensuring that the wound packing contacts all wound surfaces. This can occasionally lead to wound packing that is too tight and that may actually push the wound apart. When a wound is packed too tightly it may not be able to heal properly as it is being kept open by the packing.

The present invention includes a method that addresses the problem of excessively tight wound packing. The method comprises the steps of under-packing the wound, sealing the wound and applying suction to the wound. The under-packing is accomplished by basically loosely lining the wound with the packing material. The wound is sealed and suction is applied. With suction applied, the wound surface is forced into intimate contact with the packing material. This method enables the packing material to perform its functions without the risk of excessively tight packing and the associated deleterious wound healing issues.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A device for treating a wound, the device comprising:
    means for suctioning fluid from the wound, said means comprising:
        i) an inlet valve,
        ii) an outlet valve,
        iii) a resilient element disposed between the inlet valve and the outlet valve and responsive to a mechanical force;
    means for sealing the wound, said sealing means engaging the skin adjacent the wound, and
    means for reinforcing said sealing means, said reinforcing means coupled to said sealing means such that suction forces applied to the wound are greater than those that would be applied in the absence of said reinforcement means, said reinforcing means i) inhibiting said sealing means from deflecting into a lower portion of the wound and ii) drawing an interior portion of the wound toward said sealing means thereby increasing wound drainage and contraction.

2. The device according to claim 1, wherein said reinforcing means is semiflexible.

3. The device according to claim 1, for use with a remote source of suction, wherein said suction means is adapted for coupling to the remote source of suction.

4. The device according to claim 1, wherein each of the inlet valve and the outlet valve is a one-way valve.

* * * * *